US012085549B2

(12) United States Patent
Rivers

(10) Patent No.: US 12,085,549 B2
(45) Date of Patent: Sep. 10, 2024

(54) SYSTEM AND METHOD FOR DETERMINING THE SEX AND VIABILITY OF POULTRY EGGS PRIOR TO HATCHING

(71) Applicant: The United States of America, as represented by the Secretary of Agriculture, Washington, DC (US)

(72) Inventor: Adam R. Rivers, Gainesville, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 286 days.

(21) Appl. No.: 17/120,656

(22) Filed: Dec. 14, 2020

(65) Prior Publication Data

US 2021/0181174 A1 Jun. 17, 2021

Related U.S. Application Data

(60) Provisional application No. 62/947,681, filed on Dec. 13, 2019.

(51) Int. Cl.
*G01N 33/08* (2006.01)
*A01K 43/00* (2006.01)
*A01K 45/00* (2006.01)
*G01N 33/68* (2006.01)

(52) U.S. Cl.
CPC ............ *G01N 33/08* (2013.01); *A01K 43/00* (2013.01); *A01K 45/007* (2013.01); *G01N 33/6848* (2013.01); *G01N 2560/00* (2013.01)

(58) Field of Classification Search
None
See application file for complete search history.

(56) References Cited

PUBLICATIONS

Webster, B, et al. Avian Egg Odour Encodes Information on Embryo Sex, Fertility and Development, PLOS One, 1-10 (Year: 2015).*
Dupre, R. et al. Iterative Self-Learning: Semi-Supervised Improvement to Dataset Volumes and Model Accuracy, CVPR'2019 workshop—Uncertainty and Robustness in Deep Visual Learning, Jun. 6, 2019 (Year: 2019).*
Guo, R. et al. Spatially Weighted Principal Component Analysis for Imaging Classiication, J Comput Graph Stat. 24(1), 274-296. HHS Public Access. (Year: 2015).*
Majchrzak, T. et al. PTR-MS and GC-MS as complementary techniques for analysis of volatiles: A tutorial review, Analytica Chimica Acta 1035 (2018) 1-13 (Year: 2018).*

* cited by examiner

*Primary Examiner* — Xiaoyun R Xu
(74) *Attorney, Agent, or Firm* — John Fado; John Henri

(57) ABSTRACT

Volatile organic chemicals emitted by a shell egg embryo are used to identify the fertility, viability, and sex of the shell egg embryo. Shortly after the egg is laid, the egg is isolated in a vapor-tight compartment so that a vapor containing volatile organic chemicals emitted by the shell egg embryo collect in the headspace of the compartment. The chemicals in the vapor are analyzed to construct a chemical profile of the shell egg embryo, and then the chemical profile of the shell egg embryo vapor is loaded into a previously developed model. Based on the data generated by the model, the shell egg is embryo is predicted to be an alive male, an alive female, an infertile egg, or an egg containing a dead embryo.

9 Claims, 5 Drawing Sheets

SYSTEM AND METHOD FOR DETERMINING THE SEX AND VIABILITY OF POULTRY EGGS PRIOR TO HATCHING

REFERENCE TO RELATED APPLICATIONS

This application claims the benefit of U.S. Provisional Application No. 62/947,681, filed Dec. 13, 2019, which is incorporated herein by reference in its entirety.

FIELD OF THE INVENTION

The disclosed system and method relates to determining the sex and viability of embryos in poultry eggs prior to hatching. Specifically, the system and method described herein relates to analyzing chemicals emitted by poultry eggs, and then determining the sex and viability of the chick within the egg based on the emitted chemicals.

BACKGROUND OF THE INVENTION

There is a substantial industry associated with the production and management of egg-laying poultry. Approximately 3.2 billion egg-laying chickens are produced annually, including 380 million in the United States alone. Currently, chicks are incubated for about 21 days prior to hatching. After hatching, the chicks are examined by a specialized inspector and separated into groups of male and female chicks. Male layer chicks have no commercial value and are euthanized after their sex is determined.

Animal rights groups are strong proponents of the early identification of nonproductive (male) embryos/chicks. Chicken embryos begin sensory perception at day 7 and by day 13 the chick's neural tube has developed into a functioning brain. American Veterinary Medical Association guidelines for euthanasia in bird embryos require the use of neonate methods after 10.5 days. The earlier in the developmental process male embryos/chicks are identified, the less likely the animals are to experience pain when they are euthanized. Further, there is significant expense associated with incubating eggs containing male embryos for a full 21 days. Poultry producers could cut their incubating expenses by up to half if an early, reliable means of identifying male embryo shell eggs could be used.

The need exists for an industrial-scale process for identifying male embryos/chicks as early in the developmental process as possible. The current invention comprises a means of collecting and analyzing the chemicals emitted by shell eggs—and making a determination regarding the presence, sex, and viability of an embryo within the shell egg.

Specifically, in accordance with the preferred embodiment of the current process, the presence, sex and viability of the embryo in a shell egg is determined by statistically analyzing the relative concentrations of volatile organic compounds emitted by the egg shortly after the egg is laid. The volatile organic compounds are measured using mass spectrometry (or other chemical identification methods), and the mass-to-charge intensities are analyzed and classified using a trained machine learning model. The data processed through the model identifies/classifies the shell eggs as containing male or female embryos, and also identifies infertile eggs and eggs which contain non-viable embryos—ideally within the one to five days after laying.

SUMMARY OF THE INVENTION

This disclosure is directed to a method and apparatus for identifying the sex and viability of a shell egg prior to hatching. In accordance with the method, shortly after the egg is laid, the egg is isolated in an airtight compartment so that a vapor containing volatile organic chemicals emitted by the egg collects in the headspace of the compartment. The headspace vapor is analyzed and the chemical content/chemical profile of the vapor is determined. The chemical profile of the headspace vapor is then analyzed with a previously "trained" model. Based on the projection/data generated by the classifier/model, a decision is made regarding the sex, fertility, and viability of the chick based on the comparison.

DETAILED DESCRIPTION OF PREFERRED EMBODIMENTS

Figure 1:
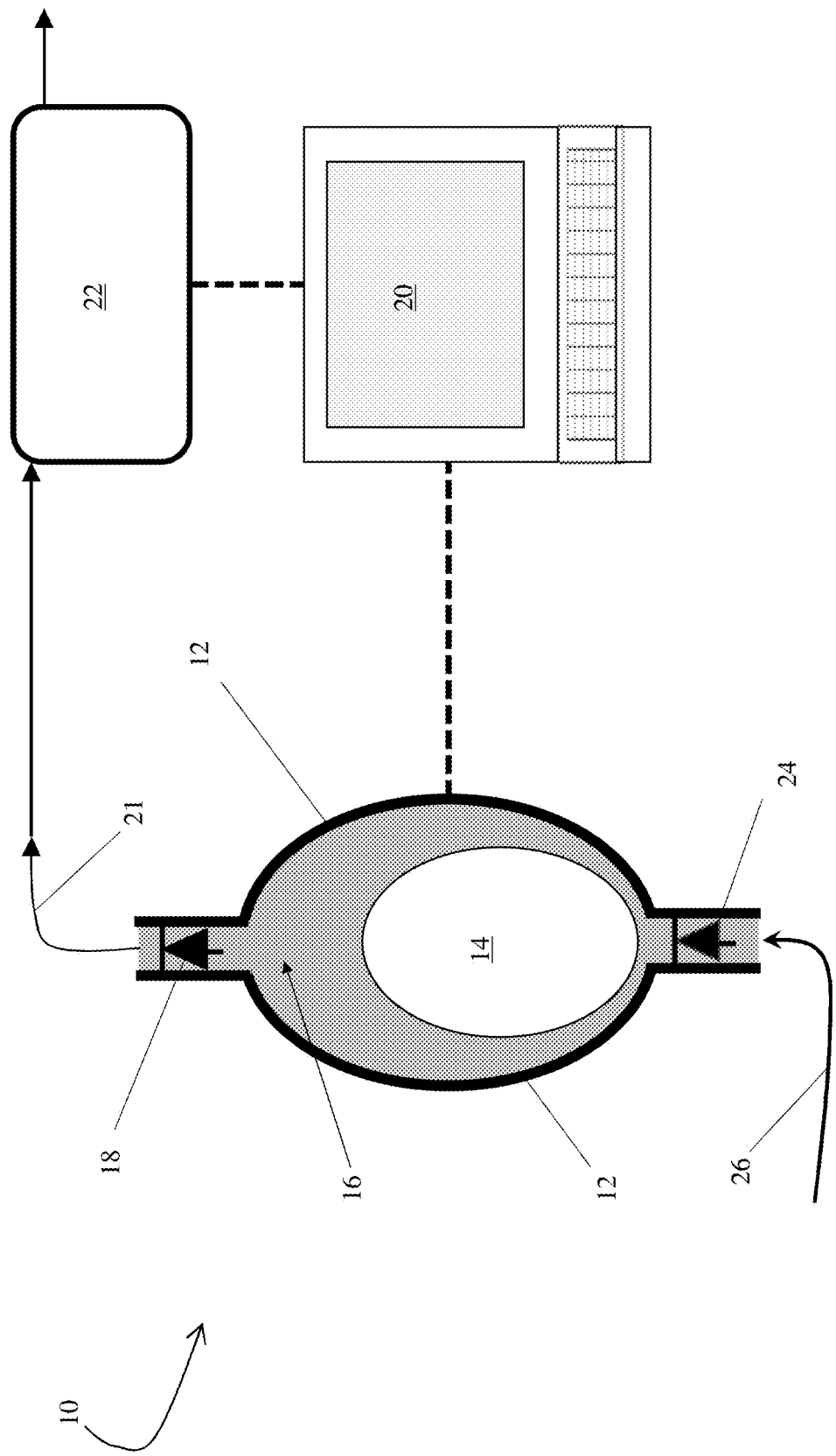
FIG. 1 is a schematic of an organic vapor sampling compartment and the associated spectrometry-type chemical analysis instrument and associated processor/controller.

As generally shown in FIG. 1, the organic vapor analysis system 10 described herein comprises (in part) an organic vapor sampling compartment 12. The vapor sampling compartment 12 is comprised of a vapor-tight structure/compartment that effectively isolates the egg 14. At the beginning of the sex determination process, an egg 14 is placed in the vapor sampling compartment 12, and volatile vapor compounds are allowed to collect in the headspace area 16 in sampling compartment 12.

For the purpose of this disclosure, the term "vapor tight compartment" means a compartment that is sufficiently sealed to allow sufficient quantities of volatile compounds to concentrate for analysis.

When the vapor sampling process is initiated, organic vapors are drawn from the headspace 16, through an upper valve 18 (preferably a check valve or other means of selectively sealing the compartment 12) and away from the compartment 12 in the direction of the arrow 21. In the preferred embodiment, the vapor is directed to vapor analysis instrumentation 22 that analyzes the vapor and directs data to a processor controller 20 which processes the data and identifies the chemicals in the vapor.

Simultaneously, as the vapor is drawn out of the compartment 12, replacement gas (preferably air) is drawn upwardly through the lower check valve 24 (or other selective sealing means) in the direction of the arrow 26 and into the compartment 12. In an alternative embodiment without a replacement gas enlet, the pressure may be reduced slightly in the compartment during sampling.

For the purposes of this disclosure, the fluid control hardware (including valves, tubing, etc.) as well as the vapor analysis device(s) (a mass spectrometer-type instrument and/or other means of analyzing the vapor) is schematically shown in FIG. 1 as vapor analysis instrumentation 22.

In the preferred embodiment, the system 10 is designed to be scaled up to evaluate multiple eggs in parallel. For example, multiple compartments 12 may be arranged in close proximity to form a unitary panel. In one alternative embodiment, multiple compartments 12 are connected and horizontally split to form an upper tray and a lower tray. The manipulation and transportation of the eggs can be accomplished through conventional egg-handling equipment currently used in industrial-scale egg operations. In additional alternative embodiments, other scaled-up configurations should be considered within the scope of the current embodiment so long as they are consistent with the ability to isolate the egg 14 as generally shown in FIG. 1.

In further alternative embodiments, spectrometer probes may be directly incorporated into the design of the upper portion of the compartment 12 to make operation more compact. In further alternative embodiments, optode-type sensors may be used in the compartment 12 headspace 16. Further, any gas analysis system known in the art may be used that is capable of providing the chemical analysis data needed to determine the chemical content of the headspace vapor so that subsequent processes can identify the sex of the shell egg embryos.

To achieve rapid vapor detection and analysis, in the preferred embodiment, an inline mass spectrometer such as a Proton Transfer Reaction Mass Spectrometer (PTR-MS) or Selected Ion Flow Tube Mass spectrometer (SIFT-MS) comprise the vapor analysis instrumentation 22 shown in FIG. 1. Vapor analysis can also be accomplished by Gas Chromatography-Mass Spectrometry. When Gas Chromatography-Mass Spectrometry (GC-MS) is used to detect sex and viability, volatile compounds are separated on a gas chromatography column, and compounds are identified by retention time and unique ion fragment patterns. The structure of the compounds does not need to be known, it only needs to be matched with retention times and fragmentation patterns identified previously and used for training the vapor chemical content database/model. The peak intensities of detected compounds are used as raw data for sex prediction.

Figure 5:
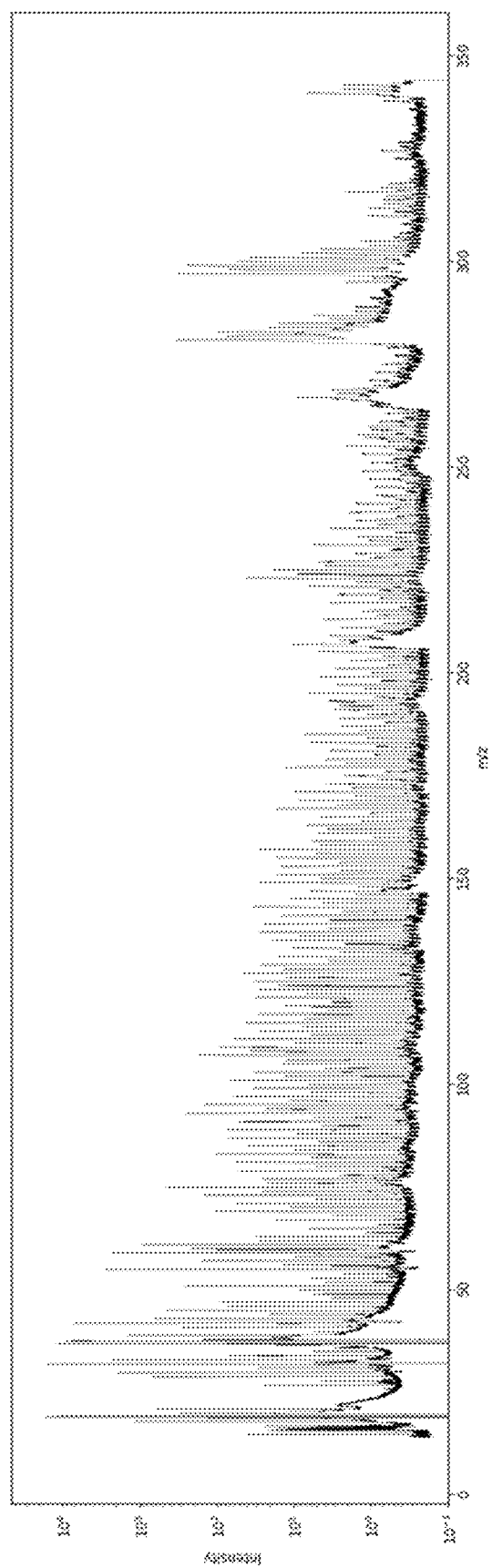
FIG. 5 is a mass spectrum of an egg collected with a proton transfer reaction mass spectrometer. A male egg at 8 days of development was placed into a jar. The headspace equilibrated for five minutes then a one second sample of the headspace air was taken.

In PTR-MS or other real-time mass spectrometry methods, there is no chromatography step. In PTR-MS, the headspace vapor is drawn into a drift tube reaction chamber within the instrument. Purified hydronium ions are reacted with the volatile headspace compounds. This soft ionization creates protonated volatile organic chemicals (VOCs) and VOC ion fragments. These ions are focused then briefly trapped in a hexapole while carrier gas is removed by the vacuum system and injected into a time of flight-type mass spectrometer. This results in a simplified mass to charge (m/z) peak pattern which can be integrated over short timescales of 0.1 second to 1 second. The result is a series of peaks and peak intensities that can be used as raw data for sex determination (FIG. 5).

Training of the Model

Once the chemicals that are present in the headspace vapor are identified, the preferred embodiment of the current invention uses an artificial intelligence-based chemical profile "model" to identify the sex and viability of the shell egg embryos and make a determination regarding the viability of the of the embryo. Specifically, the invention uses a trained supervised classification model to identify/predict the sex and viability of the shell egg embryo.

The chemical profile model was developed by collecting the volatiles spectra of eggs with known sex, fertility, and viability status. The initial iteration of the current invention used univariate feature selection and "l2" (Ridge) regularized logistic regression for training and classification. In alternative embodiments, other classifiers could also be used including but not limited to, support vector machines, feed-forward neural networks, tree-based methods, ensemble models such as random forests, or Bayesian methods such as Naive Bayesian classifiers and Bayesian networks. Semi-supervised learning methods may be applied to improve classification from customer data.

All these supervised methods rely on the collection of volatiles data from eggs of known sex and viability status as training data. In the training phase, features may be selected using one of several methods including univariate feature selection on standardized data. These data are split into testing, validation and training datasets and used to select model parameters such as regularization strength, and to evaluate model performance.

The labels for the training data (alive male, alive female, infertile, dead) are determined by one of several methods. The eggs may be incubated until later in gestation and examined. Infertile eggs will appear empty when held up to a light later in gestation (candled). Dead embryos will have a characteristic blood band around the inside of the shell 3-4 days after the eggs are laid. Sex can be determined by dissection and examination of embryo's gonads on day 18. Sex determination can also be made at any point in development by polymerase chain reaction (PCR) of a fragment of the female-specific gene SWIM6 on the W chromosome, and a fragment of the universal 12S positive control gene.

Machine Learning-Based Classification

During normal instrument operation (classification of eggs) the relative intensities representing specific compounds present in male and female, viable and nonviable embryos/chicks are collected. The signal intensities at specific mass-to-charge (m/z) ratios previously identified by the machine learning model are statistically standardized. These values are fed into the machine learning classifier which returns a multiclass probability for the 4 embryo classes (alive male, alive female, infertile, dead).

Accurate classification in new facilities or on new breeds sometimes requires controlling for systemic changes that can shift the volatiles profile. Examples of these differences include breed differences, environmental or gestational age differences. These systemic changes are known as covariate shifts. The current invention can process unlabeled data from a new location during the classification process to reweight the model to take systemic shifts into consideration. Several methods can be used for this, including batch normalization and doubly robust covariate shift correction.

Operational Process

As generally shown in FIG. 1, in operation, in the preferred embodiment, an egg 14 is isolated in the compartment 12 of the organic vapor analysis system 10 and volatile vapor compounds are allowed to collect in the headspace area 16 at the top of the sampling compartment 12. Sufficient vapor generally collects in the headspace 16 in about 5 minutes, but optimization may reduce this time.

To initiate the sampling process, a processor/controller 20 opens the check valve 18 (or a similar control valve) to allow organic vapors to be drawn from the compartment headspace 16, through the valve 18 and away from the compartment 12 in the direction of the arrow 21. Simultaneously, replacement vapor (preferably air) is drawn upwardly through the lower check valve 24 in the direction of the arrow 26 and into the compartment 12.

The organic vapor drawn from the headspace 16 is directed into vapor analysis instrumentation 22. In the preferred embodiment, the vapor analysis instrumentation 22 comprises a PTR-MS. The headspace vapor is drawn into a drift tube within the PTR-MS. Purified hydronium ions are reacted with the volatile compounds. This soft ionization creates protonated VOCs and VOC ion fragments. These ions are focused then briefly trapped while carrier gas is removed by the vacuum system and injected into a time of flight-type mass spectrometer. This results in a simplified mass to charge (m/z) peak pattern which can be integrated over short timescales of 0.1 second to 1 second.

Data regarding the relative PTR-MS intensities representing specific compounds present in male and female, viable and nonviable embryos/chicks is communicated from the PTR-MS to the controller/processor 20. The signal intensities at specific mass-to-charge (m/z) ratios (previously identified by the machine learning model) are statistically standardized. These values are fed into the machine learning classifier (i.e. model) as features of an instance. The classifier returns a multiclass probability for the 4 embryo classes (alive male, alive female, infertile, dead).

Once an egg (or multiple compartments of eggs) has been sexed, information is passed to the egg handling equipment (including automated pneumatic egg lifting systems) via compatible industrial control protocols. The egg handling system can then separate female eggs for incubation. Male, infertile and inviable eggs can be diverted to create other products.

EXAMPLES

The first example comprises a proof-of-concept investigation done by the inventors. The inventors conducted an experiment associated with this example by using 20 specific pathogen-free chicken eggs from the Leghorn breed. All eggs were analyzed (using GC-MS) to determine their volatile profiles at 3-5 days of incubation and the sex, fertility or approximately day of death was determined after that by veterinary examination.

In accordance with the current process, eggs were isolated in 237 mL (8 ounce) jars with a modified lid for insertion of solid phase microextraction (SPME) fibers. Once eggs were added to jars, lids were sealed and volatiles were allowed to permeate the headspace for 60 minutes. PDMS-DVB SPME fibers (Supelco, Bellefonte, PA, United States), were exposed to headspace volatiles for 30 min. All volatile collections were performed at 30° C. Volatiles adsorbed onto SPME fibers were thermally desorbed onto an Agilent 7890B GC coupled to a 5977A MSD (Palo Alto, CA) outfitted with an Agilent DB-1 column (60 m×0.320 mm×0.25 μm).

For further confirmation, identification, and peak resolution, additional injections were occasionally performed on an Agilent 7890B GC coupled to a 5977A MSD and outfitted with an Agilent DB-Wax column (60 m×0.320 mm×0.25 μm). Desorbed volatiles were analyzed using Retention indices (RIs) that were calculated using a homologous series of n-alkanes on both the DB-1 and DB-Wax columns. RI values from both columns were used to assist with initial identification, and identities were further confirmed by comparison to retention times and fragmentation patterns of standards. Compound identities not verified on both instruments with a commercial or other available standard were marked as tentatively identified.

To determine the sex, eggs were removed from the incubator at 18 days. The eggshells were opened, and the embryos were removed. The embryos were humanely euthanized by atlanto-occipital disarticulation. The skin was removed from the chest and abdominal regions. The chest was opened, and the viscera were removed. The gonads were examined using a dissecting loop to identify the testis or ovary. Two avian veterinarians confirmed the sex determination. There were 2 infertile eggs, 2 early dead eggs, 7 mature female and 9 mature male eggs.

Data were analyzed for sex prediction using the Scikit Learn Python package (Pedregosa et al., 2011). The peak intensities for identified compounds and the incubation day were used for learning methods. First missing data were imputed using mean value replacement for each feature. Then features were log-transformed and standardized to have a mean of 0 and standard deviation of 1. Univariate feature selection based on mutual information criterion was used to select compounds to be used in sex determination. Eight compounds were selected from 160 original volatile compounds initially detected. Those data were used to train a logistic regression model with "l2" regularization (C=1). Six-fold cross validation was used to estimate model classification accuracy. Precision-recall curves and receiver operator characteristic (ROC) curves were estimated by creating 1000, 15%/85% test/train data splits. For each split a regularized logistic regression model was trained and the test data were scored.

Results

Figure 2:
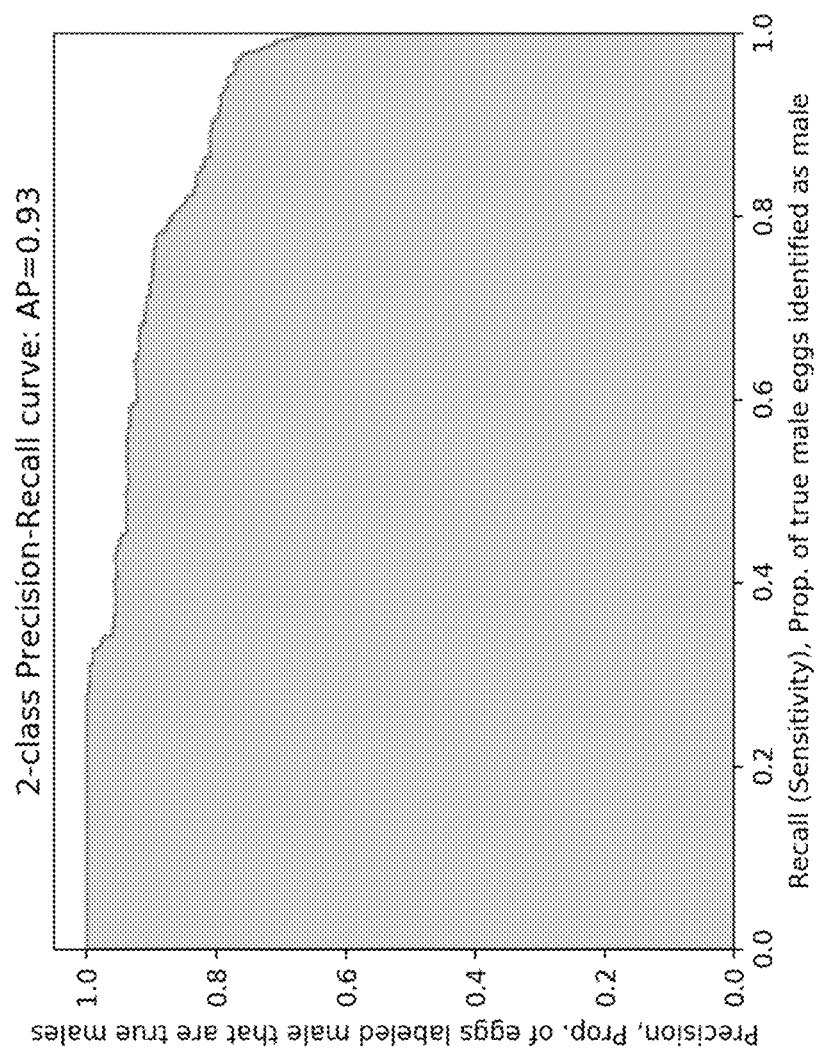
FIG. 2 is a precision-recall curve for the classifiers trained. The line represents the precision and recall (sensitivity) of the classifier as it moves along potential score cutoff values. Average precision of the classifier is 93% in the current example.

The logistic classifier was trained on the 8 selected features and performance was evaluated in several ways. The classifier had an accuracy of 96+/−19% SD when evaluated using 6-fold cross validation, where N=16 was split into 13 train and 3 test samples, 6 times. The small number of replicates is the cause of the high variability. FIG. 2 is a precision recall curve that shows graphically shows how the classifier performed across different potential thresholds. Precision-recall curves present the same data as receiver operator characteristic (ROC) curves but are more robust to skewed data.

Figure 3:
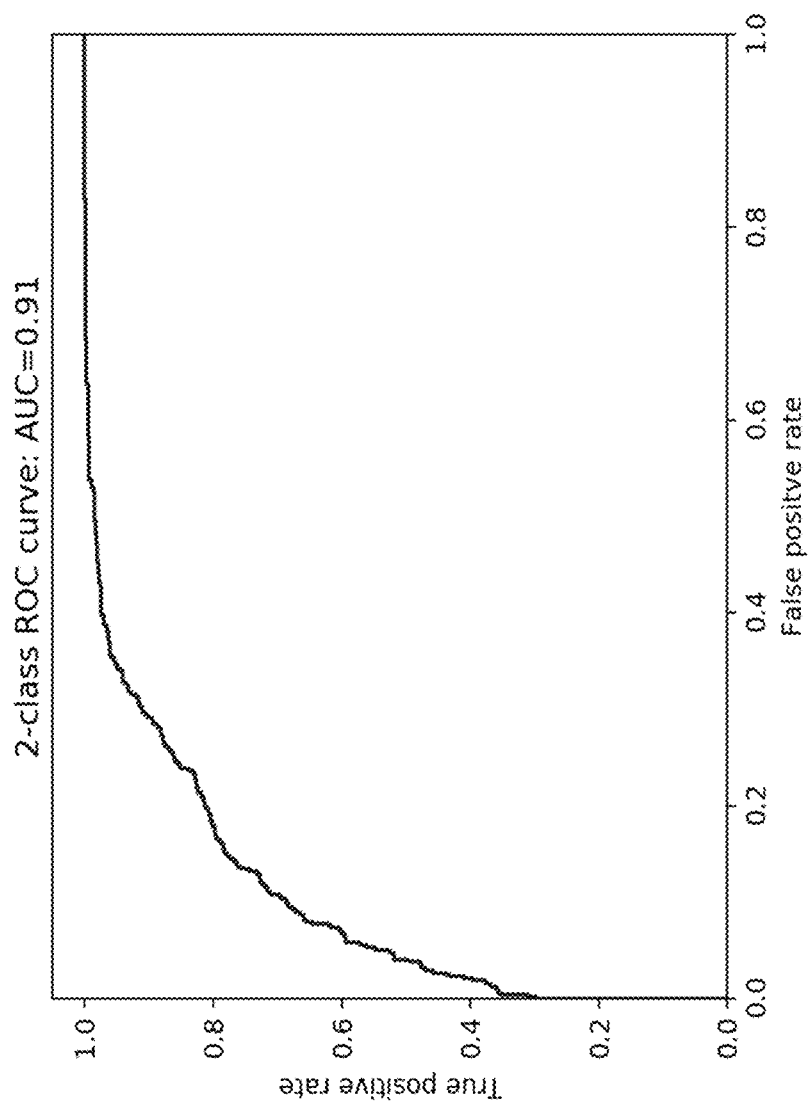
FIG. 3 is a receiver operator characteristic (ROC) curve for a logistic regression classifier trained on Gas chromatography-Mass spectrometry (GC-MS) data.

Equivalently, FIG. 3 shows that the area under the ROC curve was 0.91. The predictive power of the model is relatively high, particularly given the very small training set used. It suggests that there are key volatiles present in the data that can reliably predict sex between day 3-5.

Figure 4:
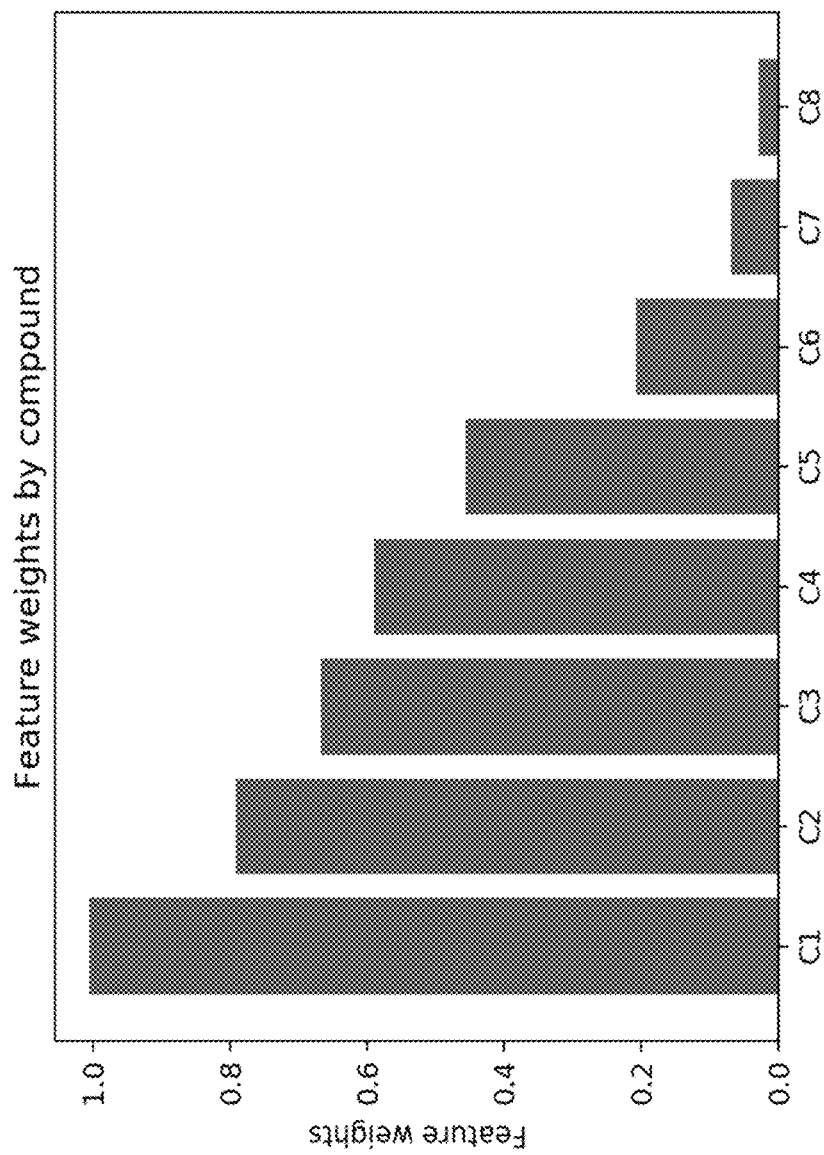
FIG. 4 is a graphical description of absolute values of weights of 8 selected compounds (C1-C8) that are strongly represented in the logistic regression model for the current example.

Of the 160 compounds collected just a few were strongly weighted in the model. The absolute value of the weights for the 8 compounds (C1-C8) selected by univariate feature selection are shown in FIG. 4. These data suggest that a small number of compounds are predictive of egg sex.

As a second example of collection methods, the spectra of an example egg was collected using an Ionicon TOF-1000 Ultra (Innsbruk, Austria) proton transfer reaction mass spectrometer (PTR-MS). A male chicken egg at day 8 of development was equilibrated in a 125 ml glass jar with a septa for 5 minutes. The intake needle of the PTR-MS was inserted, and air was drawn out for several seconds. FIG. 5. represents the spectrum of volatile components integrated over 1 second and collected at a Townsend (E/V) value of 113.0. Similar to the data described in the first example, the data collected by PTR-MS is also used as a basis to develop models for sex and viability prediction.

For the foregoing reasons, it is clear that the method and apparatus described herein provides an innovative means of identifying the sex of a poultry embryo shortly after the egg is laid. The current system may be modified in multiple ways and applied to various types of egg-laying animals. The disclosed method and apparatus may be modified and customized as required by a specific operation or application, and the individual components may be modified and defined, as required, to achieve the desired result.

Although the materials of construction are not described, they may include a variety of compositions consistent with the function described herein. Such variations are not to be regarded as a departure from the spirit and scope of this disclosure, and all such modifications as would be obvious to one skilled in the art are intended to be included within the scope of the following claims.

The amounts, percentages and ranges disclosed herein are not meant to be limiting, and increments between the recited amounts, percentages and ranges are specifically envisioned as part of the invention. All ranges and parameters disclosed herein are understood to encompass any and all sub-ranges subsumed therein, and every number between the endpoints. For example, a stated range of "1 to 10" should be considered to include any and all sub-ranges between (and inclusive of) the minimum value of 1 and the maximum value of 10 including all integer values and decimal values; that is, all sub-ranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Similarly, if the term "about" precedes a numerically quantifiable measurement, that measurement is assumed to vary by as much as 10%. Essentially, as used herein, the term "about" refers to a quantity, level, value, or amount that varies by as much 10% to a reference quantity, level, value, or amount.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The term "consisting essentially of" excludes additional method (or process) steps or composition components that substantially interfere with the intended activity of the method (or process) or composition, and can be readily determined by those skilled in the art (for example, from a consideration of this specification or practice of the invention disclosed herein). The invention illustratively disclosed herein suitably may be practiced in the absence of any element which is not specifically disclosed herein.

I claim:

1. A method of identifying the sex of a shell egg embryo, the method comprising:
    (a) isolating at least a portion of a shell egg in a vapor-tight compartment;
    (b) drawing vapor/volatiles from the vapor-tight compartment headspace so that chemicals emitted from the shell egg are present in the vapor;
    (c) analyzing the vapor emitted in step (b) to get chemical compound data that describes chemical compounds that are present in the vapor;
    (d) providing a trained and weighted predictive supervised classification model, wherein a classifier predicts the sex of the shell egg embryo from the presence and quantity of specifically weighted compounds found in the vapor emitted by the shell egg; wherein a regularized logistic regression or feed-forward neural network is trained using Mass spectrometry data, training the classifier on at least eight selected features, wherein relative intensities representing specific compounds present in male and female, viable and nonviable embryos/chicks are collected, the signal intensities at specific mass-to-charge (m/z) ratios are statistically standardized, and said values are fed into a machine learning classifier which returns a multiclass probability for four embryo classes which are alive male, alive female, infertile, dead,
    (e) inputting the chemical compound data of step (c) into the trained and weighted predictive supervised classification model provided in step (d), and getting a data output comprising shell egg embryo classification data; and,
    (f) making a prediction regarding the sex of the shell egg embryo based on the shell egg embryo classification data in step (e).

2. The method of claim 1 wherein, in step (d) the trained and weighted predictive supervised classification model is a statistical model that has been previously trained using chemical profiles of shell eggs with known sex, fertility, and viability.

3. The method of claim 2 wherein the trained and weighted predictive supervised classification model is iteratively improved through semi-supervised learning from unlabeled shell eggs that have been classified.

4. The method of claim 1 wherein, in step (c), the vapor is analyzed by vapor analysis instrumentation.

5. The method of claim 1 wherein in step (c), the vapor is analyzed by a mass spectrometer.

6. The method of claim 1 wherein, in step (c), the vapor is analyzed by at least one of a PTR-MS, a SIFT-MS, or a GC-MS.

7. The method of claim 1 wherein a processor/controller controls the processes described in steps (b)-(e).

8. The method of claim 1 wherein the trained and weighted predictive supervised classification model of step (d) is electronically stored on a processor/controller, the processor controller processing the chemical compound data and providing the shell egg embryo classification data output of step (e).

9. A system for determining the sex of a shell egg embryo, the system comprising:
    a vapor-tight egg compartment assembly enclosing an egg;
    a proton transfer reaction mass spectrometer (PTR-MS) in fluid communication with the vapor-tight egg compartment;
    a processor/controller in electronic communication with the PTR-MS;
    a database stored in/on the processor/controller, the database comprising chemical profiles for embryo classes alive male, alive female, infertile, dead;
    wherein the processor/controller directs vapor from the vapor-tight egg compartment to the PTR-MS to determine the chemical profile of the shell egg embryo in the vapor-tight egg compartment; signal intensities at specific mass-to-charge (m/z) ratios previously identified by the machine learning model are statistically standardized and signal intensity values are fed into a machine learning classifier; wherein a regularized logistic regression or feed-forward neural network is trained using Mass spectrometry data, training the classifier on at least eight selected features, wherein relative intensities representing specific compounds present in male and female, viable and nonviable embryos/chicks are collected, the signal intensities at specific mass-to-charge (m/z) ratios are statistically standardized, and said values are fed into a machine learning classifier which returns a multiclass probability for four embryo classes which are alive male, alive female, infertile, dead.

* * * * *